United States Patent [19]

Förster et al.

[11] Patent Number: 4,889,946
[45] Date of Patent: Dec. 26, 1989

[54] PHENOXYBENZOIC ACID COMPOUNDS AND HERBICIDAL AND PLANT GROWTH REGULANT COMPOSITIONS

[75] Inventors: Heinz Förster, Wuppertal; Ludwig Eue, Leverkusen; Robert R. Schmidt, Cologne; Klaus Lürssen, Gladbach, all of Fed. Rep. of Germany

[73] Assignee: Bayer Aktiengesellschaft, Leverkusen, Fed. Rep. of Germany

[21] Appl. No.: 404,948

[22] Filed: Aug. 4, 1982

Related U.S. Application Data

[62] Division of Ser. No. 211,990, Dec. 1, 1980, abandoned.

[30] Foreign Application Priority Data

Dec. 14, 1979 [DE] Fed. Rep. of Germany ..... 29504016

[51] Int. Cl.[4] ............................................. C07C 79/46
[52] U.S. Cl. ..................... 560/21; 558/257; 564/166; 71/111; 71/118; 71/98; 71/100; 548/378
[58] Field of Search .................. 560/21; 548/378, 378; 557/257; 564/166; 71/111, 100, 98

[56] References Cited

U.S. PATENT DOCUMENTS 3,282,991 11/1966 Klein et al. ........................ 260/101

FOREIGN PATENT DOCUMENTS 2058055 4/1979 United Kingdom ................ 560/21

Primary Examiner—Paul J. Killos
Attorney, Agent, or Firm—Felfe & Lynch

[57] ABSTRACT

Novel phenoxybenzoic acid derivatives of the general formula

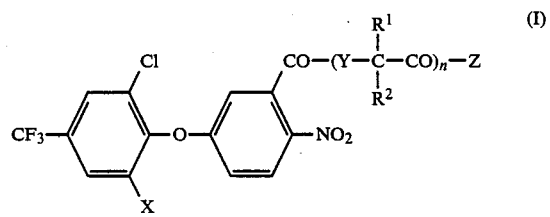

in which
R[1] and R[2], independently of one another, each represent hydrogen or methyl,
n represents zero or 1,
x represents hydrogen or chlorine,
y represents oxygen, sulphur, imino (NH) or alkylimino (N-alkyl) and
z has the meaning given in the specification, a process for the preparation of the novel compounds and their use as herbicides and plant growth regulators.

22 Claims, No Drawings

PHENOXYBENZOIC ACID COMPOUNDS AND HERBICIDAL AND PLANT GROWTH REGULANT COMPOSITIONS

This is a divisional application of Ser. No. 211,990 filed Dec. 1, 1980, now abandoned.

This invention relates to certain new phenoxybenzoic acid compounds. In additional aspect the invention relates to herbicidal compositions containing such compounds and to herbicidal methods employing such materials. In still further aspect, the invention relates to plant growth regulant compositions and method employing such compounds.

It is known that certain phenoxybenzoic acid derivatives have herbicidal properties (see DE-OS German published specification 2,311,638 and U.S. Pat. No. 3,928,416). The action of these substances is good when they are used in accordance with the pre-emergence method. However, the disadvantage is that some problem broad-leaved weeds and some graminaceous weeds are not always combated completely.

The present invention now provides, as new compounds, the phenoxybenzoic acid derivatives of the general formula

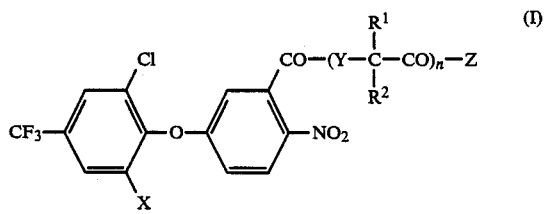

in which
$R^1$ and $R^2$, independently of one another, each represent hydrogen or methyl,
n represents zero or 1,
X represents hydrogen or chlorine,
Y represents oxygen, sulphur, imino (NH) or alkylimino (N-alkyl) and
Z represents the radical

wherein
$R^3$ and $R^4$, independently of one another, each represent an optionally substituted radical from the series alkyl, alkenyl, alkynyl, aryl, aralkyl and cycloalkyl, provided that $R^3$ or $R^4$ can be optionally substituted alkenyl or optionally substituted alkynyl only when n is 1, or
$R^3$ and $R^4$ together with the N atom to which they are bonded, represent an optionally substituted, saturated or unsaturated, optionally benzo-fused monocyclic or bicyclic radical, which optionally contains 1 to 3 further N atoms or an oxygen or sulphur atom as hetero-atom(s), or
Z, provided that n represents 1, represents an optionally substituted radical from the series alkoxy, alkenoxy, alkynoxy, aralkoxy and aryloxy, or hydroxyl or OM,
wherein
M represents one alkali metal ion equivalent or alkaline earth metal ion equivalent or optionally substituted ammonium.

The invention also provides a process for the preparation of a phenoxybenzoic acid derivative of the general formula (I), in which a phenoxybenzoic acid chloride of the general formula

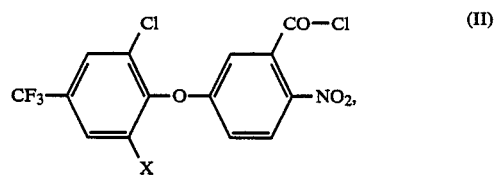

in which X has the meaning indicated above, is reacted with a compound of the general formula

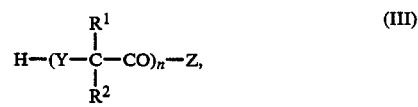

in which $R^1$, $R^2$, n, Y and Z have the meanings indicated above,
if appropriate in the presence of an acid acceptor and if appropriate using a diluent It has been found that the phenoxybenzoic acid derivatives of the formula (I) are distinguished by an outstanding herbicidal and plant growth-regulating activity. The active compounds according to the invention can be employed, in particular, for combating broad-leaved weeds and graminaceous weeds in important crops, such as, for example, in cereals and in soya beans, by the pre-emergence method. The plant growth-regulating action of the new compounds can be utilised, in particular, in their application as defoliants for cotton or for potato vein desiccation.

Surprisingly, the phenoxybenzoic acid derivatives of the formula (I) according to the invention exhibit a considerably better herbicidal and plant growth-regulating activity than the compounds of analogous structure and the same type of action which are known from the state of the art.

Formula (I) provides a definition of the phenoxybenzoic acid derivatives according to the invention. Preferably, in this formula,
$R^1$, $R^2$, n, X and Y have the meanings indicated above and
Z represents the radical

in which
$R^3$ and $R^4$, independently of one another, each represent alkyl, cyanoalkyl, alkoxyalkyl, alkylthioalkyl or dialkylaminoalkyl, with in each case up to 10 carbon atoms, cycloalkyl with up to 12 carbon atoms, aralkyl with 1 or 2 carbon atoms in the alkyl part and 6 or 10 carbon atoms in the aryl part, which is optionally substituted by halogen, aryl with 6 or 10 carbon atoms, it being possible for the aryl radical to be substituted by 1 to 3 halogen atoms, 1 to 3 alkyl groups with in each case 1 to 4 carbon atoms, trifluoromethyl, nitro, cyano or alkoxy with 1 to 4 carbon atoms, or, provided that n represents 1, alkenyl with up to 10 carbon atoms or alkynyl with up to 10 carbon atoms, or $R^3$ and $R^4$, together with the nitrogen atom to which they are bonded, form an optionally partially unsaturated and/or benzo-fused monocyclic or bicyclic radical which has up to 15 carbon atoms and is optionally substituted by 1 to 3 alkyl groups with in each case 1 to 5 carbon atoms or by two geminal alkoxy groups with in each case 1 to 3 carbon atoms, or is optionally substituted by a dioxolanylidene or dioxanylidene radical linked in a spirocyclic-like manner, or $R^3$ and $R^4$, together with the nitrogen atom to which they are bonded, form a monocyclic radical which has up to 8 carbon atoms and is optionally substituted by 1 to 3 alkyl groups with in each case 1 to 5 carbon atoms, by phenyl, which is optionally substituted by $C_1$–$C_4$-alkyl, $C_1$–$C_4$-alkoxy, halogen, trifluoromethyl, cyano or nitro, or by benzyl or phenylethyl and is optionally saturated and optionally contains a further nitrogen atom, oxygen atom or sulphur atom, or $R^3$ and $R^4$, together with the nitrogen to which they are bonded, form an unsaturated five-membered heterocyclic ring which contains up to 4 ring nitrogen atoms and is optionally substituted by $C_1$–$C_4$-alkyl, $C_{1;l}$ –$C_4$-alkoxy, $C_1$–$C_4$-alkylthio, phenyl, halogen, halogenomethyl, cyano, $C_1$–$C_4$-alkonoyl or $C_1$–$C_4$-carbalkoxy, or Z, provided that n represents 1, represents alkoxy, cyanoalkoxy, alkoxyalkoxy, alkylthioalkoxy, dialkylaminoalkoxy, alkenoxy or alkynoxy, in each case with up to 10 carbon atoms, aralkoxy with 1 or 2 carbon atoms in the alkyl part and 6 or 10 carbon atoms in the aryl part, which is optionally substituted by halogen, or aryloxy with 6 or 10 carbon atoms, it being possible for the aryl radical to be substituted by 1 to 3 halogen atoms, 1 to 3 alkyl groups with in each case 1 to 4 carbon atoms, trifluoromethyl, nitro, cyano or alkoxy with 1 to 4 carbon atoms.

Particularly preferred phenoxybenzoic acid derivatives of the formula (I) are those in which $R^1$ represents hydrogen, $R^2$ represents hydrogen or methyl, n represents zero or 1, X represents hydrogen or chlorine, Y represents oxygen, imino (NH) or methylimino (NCH$_3$) and Z represents the radical $$-N\begin{matrix}R^3\\R^4\end{matrix}$$

wherein $R^3$ represents $C_1$–$C_5$-alkyl, cyanoethyl, $C_1$–$C_4$-alkoxyethyl, 1-methyl-propargyl, 1,1-dimethylpropargyl, cyclopentyl, cyclohexyl, phenyl or benzyl, or, provided that n represents 1, allyl or propargyl, and $R^4$ represents $C_1$–$C_5$-alkyl, cyanoethyl, $C_1$–$C_4$-alkoxyethyl, 1-methyl-propargyl, 1,1-dimethylpropargyl, cyclopentyl, cyclohexyl, benzyl, naphthyl or phenyl (which is optionally substituted by 1 to 3 radicals selected from methyl, chlorine, cyano, nitro and methoxy), or, provided that n presents 1, allyl or propargyl, or wherein $R^3$ and $R^4$, together with the nitrogen atom to which they are bonded, represent pyrrolidyl, monoalkylpyrrolidyl or dialkyl-pyrrolidyl with 1 to 3 carbon atoms per alkyl group, morpholinyl or dialkylmorpholinyl with 1 to 3 carbon atoms per alkyl group, piperidyl, monoalkyl-, dialkyl- or trialkylpiperidyl with 1 to 3 carbon atoms per alkyl group, 4,4-dialkoxy-piperidyl with 1 to 3 carbon atoms per alkoxy group, spiro-substituted piperidyl of the formula $$-N\underset{\diagdown}{\diagup}\overset{O}{\underset{O}{\diagdown\diagup}}(CH_2)_m$$

wherein m represents 2 or 3, or perhydroazepinyl (the hexamethyleneimino radical), trimethyl-perhydroazepinyl, the heptamethyleneimino radical, the dodecamethyleneimino radical, 1,2,3,4-tetrahydroindolyl, monoalkyl-, dialkyl- or trialkyl-1,2,3,4-tetrahydroindolyl with up to 3 carbon atoms per alkyl group, perhydroindolyl, monoalkyl-, dialkyl- or trialkyl-perhydroindlyl with 1 to 3 carbon atoms per alkyl group, 1,2,3,4-tetrahydroquinolyl or 1,2,3,4-tetrahydrolisoquinolyl, monoalkyl-, dialkyl- or trialkyl-1,2,3,4-tetrahydroquinolyl or -iso-quinolyl with 1 to 3 carbon atoms per alkyl group, perhydroquinolyl or perhydroiso-quinolyl, monalkyl-, dialkyl- or trialkyl-perhydroquinolyl or -perhydroisoquinolyl with 1 to 3 carbon atoms per alkyl group, perhydrothioazolyl, perhydrooxazolyl, per hydrooxazinyl or the radical $$-N\diagup\overline{\diagdown}N-R'$$

wherein

R' represents $C_1$–$C_4$-alkyl, phenyl (which optionally carries one or more substituents selected from $C_1$–$C_2$-alkyl, $C_1$–$C_2$-alkoxy, fluorine, chlorine, bromine, trifluoromethyl and nitro), benzyl or phenylethyl, or wherein $R^3$ and $R^4$, together with the nitrogen atom to which they are bonded, represent the radical $$-N\diagup\overline{\diagdown}\begin{matrix}CH_2\\\\CH_3\end{matrix}\diagdown\diagup\begin{matrix}CH_3\\CH_3\end{matrix}$$

or wherein $R^3$ and $R^4$, together with the nitrogen atom to which they are bonded, represent pyrrolyl, pyrazolyl, imidazolyl, 1,2,4-triazol-1-yl, 1,2,3-triazol-1-yl, 1,3,4-triazol-1-yl or 1,2,3,4-tetrazol-1-yl, in each case optionally substituted by $C_1$-$C_3$-alkyl, $C_1$-$C_3$-alkoxy, $C_1$-$C_3$-alkylthio, phenyl, chlorine, bromine, iodine, trifluoromethyl, cyano, acetyl, carbomethoxy or carbethoxy, or wherein Z, provided that n represents 1, represents alkoxy, alkenoxy or alkynoxy, in each case with up to 5 carbon atoms.

If 5-(2,6-dichloro-4-trifluoromethyl-phenoxy)-2-nitrobenzoic acid chloride and N-methyl-aniline are used as starting substances in the process according to the invention, the course of the reaction can be represented by the following equation:

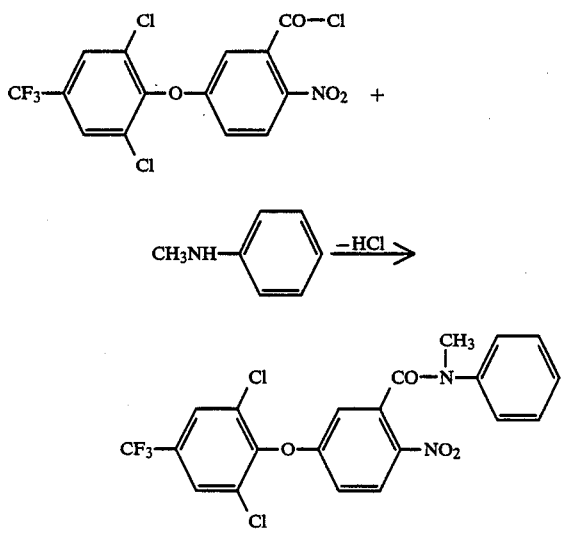

The formula (II) provides an unabiguous definition of the phenoxybenzoic acid chlorides required as starting substances in the process according to the invention. In this formula, X represents hydrogen or chlorine.

Examples of the phenoxybenzoic acid chlorides of the formula (II) which may be mentioned are 5-(2-chloro-4-trifluoromethyl-phenoxy)-2-nitro-benzoic acid chloride and 5-(2,6-dichloro-4-trifluoromethyl-phenoxy)-2-nitrobenzoic acid chloride.

The phenoxybenzoic acid chlorides of the formula (II) have not hitherto been described in the literature. However, they are obtained in a simple manner by a process in which phenoxybenzoic acids of the general formula

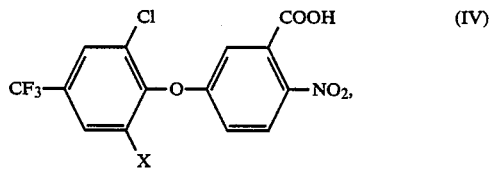

in which X represents hydrogen or chlorine, are reacted with chlorinating agents, for example thionyl chloride, if appropriate using a catalyst, for example dimethylformamide, and if appropriate using a diluent, for example 1,2-dichloroethane, at temperatures between 10° and 100° C., and the volatile components are then distilled off under reduced pressure.

The phenoxybenzoic acids of the formula (IV), that is to say 5-(2-chloro-4-trifluoromethyl-phenoxy)-2-nitrobenzoic acid and 5-(2,6-dichloro-4-trifluoromethylphenoxy)-2-nitro-benzoic acid, are already known (see U.S. patent specification No. 3,928,416).

Formula (III) provides a definition of the compounds also required as starting substances in the preparative process according to the invention. In this formula, $R^1$, $R^2$, n, Y and Z have the same preferred or particularly preferred meanings which are given above as preferred or as particularly preferred in the definition of the corresponding symbols in the formula (I).

Examples of the starting substances of the formula (III) which may be mentioned are: (a): (n=0) dimethylamine, diethylamine, di-n-propylamine, di-iso-propylamine, di-n-butylamine, di-isobutylamine, methylethylamine, methyl-n-propylaine, methyl-isopropylamine, methyl-n-butylamine, methyl-isobutylamine, methyl-sec.-butylamine, ethyl-n-propylamine, ethyl-isopropylamine, ethyl-n-butylamine, ethyl-iso-butylamine, ethyl-sec.-butylamine, propyl-butylamine, propyl-isobutylamine, propyl-sec.-butylamine, dicyclopentylamine, dicyclohexylamine, N-methyl-cyclopentylamine, N-methyl-cyclohexylamine, N-ethyl-cyclopentylamine, N-ethyl-cyclohexylamine, dibenzylamine, N-methyl-benzylamine, N-ethyl-benzylamine, N-propyl-benzylamine, N-butyl, benzylamine, N-methyl-1-naphthylamine, N-methyl-2-naphthylamine, N-methyl-aniline, N-ethyl-aniline, N-n-propyl-aniline, N-iso-propyl-aniline, N-n-butyl-aniline, N-iso-butyl-aniline, N-sec.-butyl-aniline, N-methyl-(2-methyl-phenyl)-amine, N-methyl-(3-methyl-phenyl)-amine, N-methyl-(4-methyl-phenyl)-amine, N-methyl-(3-nitro-6-methyl-phenyl)-amine, N-benzylaniline, piperidine, 2-methyl-, 3-methyl-, 4-methyl-, 2,4-dmethyl-, 2,4,6-trimethyl-, 2-ethyl-, 4-ethyl, 2,4-diethyl, 2,5-dimethyl-, 2-methyl-5-ethyl- and 2,4,6-triethyl-piperidine, pyrrolidine, 2-methylpyrrolidine, 2,4-dimethyl-pyrrolidine, 1,2,3,4-tetrahydroindoline, 2-methyl-1,2,3,4-tetrahydroindoline, parhydroindoline, 2-methyl-perhydroindoline, 2,2-dimethyl-perhydroindoline, 1,2,3,4-tetrahydroquinoline, 2-methyl-1,2,3,4-tetrahydroquinoline, perhydroquinoline, 2-methylperhydroquinoline, 1,2,3,4-tetrahydro-iso-quinoline, perhydroisoquinoline, morpholine, 3-methyl-morpholine, 3,5-dimethyl-morpholine, perhydroazepine, 3,3,5-trimethylperhydroazepine, N-methyl-piperazine, N-phenyl-piperazine, pyrazole, 3,5-dimethyl-pyrazole, imidazole, 1,2,3-triazole, 1,2,4-triazole and 1,3,4-triazole; and (b): (n=1) the methyl esters, ethyl esters, n-propyl esters, iso-propyl esters, n-butyl esters, iso-butyl esters and sec.-butyl esters of hydroxyacetic acid and hydroxypropionic acid, hydroxyacetic acid dimethylamide, diethylamide, di-n-propylamide, di-iso-propylamide, di-n-butylamide, di-iso-butylamide, N-methyl-ethylamide, N-methyl-n-propylamide, N-methyl-iso-propylamide, N-methyl-n-butylamide, N-methyl-iso-butylamide, N-methyl-sec.-butylamide, N-ethyl-n-propylamide, N-ethyl-iso-propylamide, N-ethyl-n-butylamide, N-ethyl-iso-butylamide, N-ethyl-sec-butylamide, N-propyl-n-butylamide, N-propyl-iso-butylamide, N-propyl-sec.-butylamide, diallylamide, N-methyl-allylamide, N-ethyl-allylamide, N-propyl-allylamide, N-iso-propylallylamide, N-butyl-allylamide, N-iso-butyl-allylamide, N-sec.-butyl-allylamide, N-methylpropargylamide, N-ethyl-propargylamide, N-propyl-propargylamide, N-iso-butyl-propargylamide, N-sec.-butyl-propargylamide, N-methyl-(1-methylpropargyl)-amide, dipropargylamide, dicyclopentylamide, dicyclohexylamide, N-methyl-cyclopentylamide, N-methyl-cyclohexylamide, N-ethyl-cyclopentylamide, N-ethyl-cyclohexylamide, dibenzylamide, N-methyl-benzylamide, N-ethyl-benzylamide, N-propyl-benzylamide, N-butyl-benzylamide, N-allyl-benzylamide, N-propargylbenzylamide, N-methyl-1-naphthylamide, N-methyl-2-napthylamide, N-methyl-anilide, N-ethyl-anilide, N-propyl-anilide, N-iso-propyl-anilide, N-butyl-anilide, N-isobutyl-anilide, N-sec.-butyl-anilide, N-methyl-(2-methyl-phenyl)-amide, N-methyl-(3-methyl-phenyl)-amide, N-methyl-(4-methylphenyl)-amide, N-methyl-(3-nitro-6-methyl-phenyl)-amide, N-benzyl-anilide, piperidide, 2-methyl-, 3-methyl-, 4-methyl-, 2,4-dimethyl-, 2,4,6-trimethyl-, 2-ethyl-, 4-ethyl-, 2,4-diethyl-, 3,5-dimethyl-, 2-methyl-5-ethyl- and 2,4,6-triethyl-piperidide, pyrrolidide, 2-methylpyrrolidide, 2,4-dimethyl-pyrrolidide, 1,2,3,4-tetra-hydro-indolide, 2-methyl-1,2,3,4-tetrahydro-indolide, perhydroindlide, 2-methyl-perhydroindlide, 2,2-dimethylperhydroindolide, 1,2,3,4-tetrahydroquinolide, 2-methyl-1,2,3,4-tetrahydroquinolide, perhydroquinolide, 2-methylperhydroquinolide, 1,2,3,4-tetrahydroisoquinolide, perhydroisoquinolide, morpholide, 3-methyl-morpholide, 3,5-dimethyl-morpholide, hexamethyleneamide, 3,3,5-trimethyl-hexamethyleneamide, N-methyl-piperazide, N-phenylpiperazide, pyrazolide, 3,5-dimethyl-pyrazolide, imidazolide, 1,2,3-triazolide, 1,2,4-triazolide and 1,3,4-triazolide, and the methyl esters, ethyl esters, n-propyl esters, isopropyl esters, n-butyl esters, isobutyl esters and sec.-butyl esters of aminoacetic acid, α-aminopropionic acid and N-methylaminoacetic acid.

The compounds of the formula (III) in which n represents zero are widely known base chemicals (group (a) of the examples).

α-Hydroxy-, α-mercapto- and α-amino-carboxylic acid derivatives group (b) of the examples) are also widely known compounds of the formula (III) and can be prepared by customary processes.

The α-hydroxy-carboxylic acid amides of the general formula

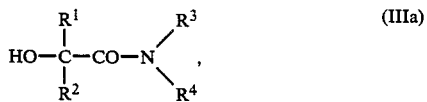

in which R¹, R², R³ and R⁴ have the meanings indicated above, some of which have not hitherto been described in the literature, are obtained, for example, by a process in which α-halogeno-carboxylic acid amides of the general formula

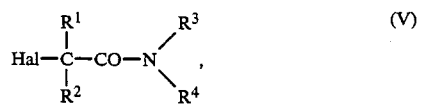

in which
R¹, R², R³ and R⁴ have the meanings indicated above and
Hal represents chlorine or bromine,
are reacted, in a first stage, with excess sodium acetate or potassium acetate, if appropriate in the presence of a catalyst, for example tetrabutylammonium bromide, and if appropriate using a diluent, for example acetic acid or toluene, at temperatures between 20° And 200° C., and the resulting acetoxy-carboxylic acid amides of the general formula

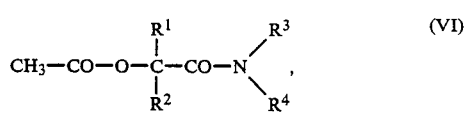

in which R¹, R², R³ and R⁴ have the meanings indicated above, is deacylated, in a second state, by reaction with dilute aqueous-alcholic sodium hydroxide solution at temperatures between 20° and 150° C. (see DE-OS (German Published Specification) 2,201,432 and U.S. patent specification No. 3,399,988).

The α-halogenocarboxylic acid amides of the formula (V) are known, or they can be prepared by processes analogous to known processes. They are obtained, for example, by reacting α-halogeno-carboxylic acid halides, for example chloroacetyl chloride, with open-chain or cyclic, aliphatic or aromatic amines, if appropriate in the presence of an acid acceptor, such as, for example, potassium hydroxide (see J. Agric. Food Chem. 4 (1956), 518–522).

The process according to the invention for the preparation of the compounds of the formula (I) is preferably carried out using a diluent. Possible diluents are virtually any of the inert organic solvents. These include, as preferences, aliphatic and aromatic, optionally halogenated hydrocarbons, such as pentane, hexane, heptane, cyclohexane, petroleium ether, benzine, ligroin, benzene, toluene, xylene, methylene chloride, ethylene chloride, chloroform, carbon tetrachloride, chlorobenzene and o-dichlorobenzene; ethers, such as diethyl ether, dibutyl ether, glycol dimethyl ether, diglycol dimethyl ether, tetrahydrofuran and dioxan; ketones, such as acetone, methyl ethyl ketone, methyl isopropyl ketone and methyl isobutyl ketone; esters, such as methyl acetate and ethyl acetate; nitriles, for example acetonitrile and propionitrile; amides, for example dimethylformamide, dimethylacetamide and N-methylpyrrolidone; and dimethylsulphoxide, tetramethylene sulphone and hexamethylphosphoric acid triamide.

Acid acceptors which can be used are any of the customary acid-binding agents. Acid-binding agents which have provided particularly suitable are alkali metal hydroxides, for example sodium hydroxide and potassium hydroxide; alkali metal carbonates, such as sodium carbonate and potassium carbonate; alkali metal alcoholates, for example sodium methylate or ethylate and potassium methylate or ethylate; and aliphatic, aromatic or heterocyclic amines, for example triethylamine, trimethylamine, dimethylaniline, dimethylbenzylamine and pyridine.

The reaction temperature can be varied within a substantial range. In general, the reaction is carried out between −20° and 100° C., preferably between 0° and 50° C.

The reaction according to the invention is in general carried out under normal pressure.

The starting substances are usually employed in approximately equimolar amounts for carrying out the process according to the invention. The reaction is in general carried out in a suitable diluent in the presence of an acid acceptor, and the reaction mixture is stirred at the required temperature for several hours. An organic solvent, for example toluene, is then added and the organic phase is worked up in the customary manner by washing and drying and distilling off the solvent.

The new compounds are in some cases obtained in the form of oils, some of which cannot be distilled without decomposition, but which can be freed from the last volatile constituents by so-called "incipient distillation", that is to say by prolonged heating to moderately elevated temperatures under reduced pressure, and they can be purified in this manner. They are characterised by their refractive index. If the new products are obtained in solid form, they can be purified by recrystallisation. They are then characterised by their melting point.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentration, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, caca plantations, soft fruit plantings and hopfields, and for the selective combating of weeds in annual cultures.

The active compounds according to the invention also have a very good plant growth-regulating activity. They are particularly suitable for growth inhibition and for defoliation and desiccation of the leaves of cotton and potatoes.

The active compounds can be converted into the customary formulations, such as solutions, emulsions, wettable powders, suspensions, powders, dusting agents, soluble powders, granules, suspension-emulsion concentrates, natural and synthetic materials impregnated with active compound, and very fine capsules in polymeric substances.

These formulations are produced in known manner, for example by mixing the active compounds with extenders, that is to say liquid or solid carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromtic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used round natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dye-stuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, and granules. They may be used in the customary manner, for example by watering, spraying, atomising or scattering The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.05 and 10 kg of active compound per hectare, preferably between 0.1 and 5 kg/ha.

The present invention also provides a herbicidal or plant-growth-regulating composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the compounds according to the invention is illustrated in the following examples.

PREPARATIVE EXAMPLES

Example 1

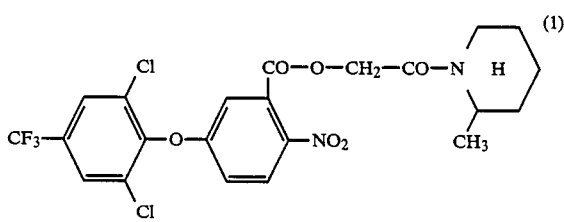

6.6 g of hydroxyacetic acid 2-methylpiperidide were initially introduced into 60 ml of toluene, together with 8 ml of pyridine. 2-Nitro-5-(2,6-dichloro-4-trifluoromethyl-phenoxy)-benzoic acid chloride, dissolved in 30 ml of toluene, was added dropwise at 0° C. The mixture was then stirred at 20° C. for 12 hours. 100 ml of toluene were subsequently added and the organic phase was washed with an alkali, and then with water until neutral. The toluene was distilled off. 14.8 g (70% of theory) of 5-(2,6-dichloro-4-trifluoromethyl-phenoxy)-2-nitrobenzoic acid 2-methyl-piperidyl-carbonylmethyl ester with a melting point of 50° C. remained.

Example 2

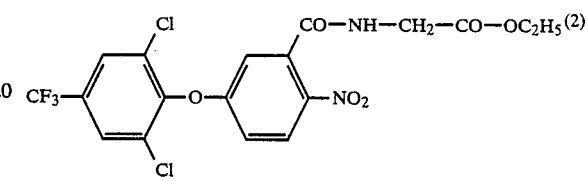

7 g of aminoacetic acid ethyl ester chloride, 20.7 g of 2-nitro-5-(2,6-dichloro-4-trifluoromethyl-phenoxy)-benzoic acid chloride and 180 ml of acetonitrile were initially introduced into the reaction vessel. 4 g of sodium hydroxide, dissolved in 10 ml of water, were added dropwise at −10° to −5° C. The reaction mixture was then poured onto water and adjusted to pH 10 and the crystalline product was filtered off. 23 g (95% of theory) of 5-(2,6-dichoro-4-trifluoromethyl-phenoxy)-2-nitro-benzoic acid (ethoxycarbonylmethyl)-amide with a melting point of 146° C. were obtained.

Example 3

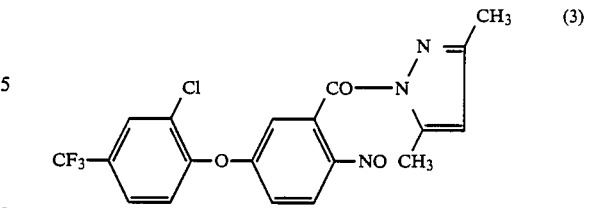

6 g of 3,5-dimethylpyrazole, 6.3 g of triethylamine and 90 ml of toluene were initially introduced into the reaction vessel. 25 g of 2-nitro-5-(2-chloro-4-trifluoromethyl-phenoxy)-benzoic acid chloride, dissolved in 50 ml of toluene, were added dropwise at 0-5° C. The mixture was stirred at 20° C. for 12 hours. 100 ml of toluene were then added and the organic phase was washed once with an acid and once with an alkali and then with water until neutral. The toluene was distilled off. An oil which slowly crystallised remained. 25 g (88% of theory) of 5-(2-chloro-4-trifluoromethyl-phenoxy)-2-nitro-benzoic acid 3,5-dimethyl-pyrazolide with a melting point of 123°-124° C. were obtained.

The following compounds could be prepared analogously to one of the Examples 1 to 3:

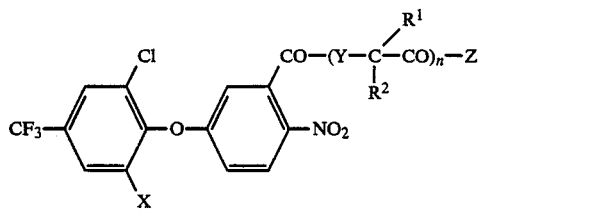

| Example No. | R¹ | R² | n | X | Y | Z | Yield (% of theory) | Physical data (refractive index; melting point °C.) |
|---|---|---|---|---|---|---|---|---|
| 4 | H | H | 1 | H | O | OCH$_3$ | 92 | $n_D^{20}$: 1.5426 |
| 5 | H | H | 1 | H | O | OC$_2$H$_5$ | 88 | $n_D^{20}$: 1.5354 |
| 6 | H | H | 1 | H | O | OC$_4$H$_9$—n | 92 | resin |
| 7 | H | CH$_3$ | 1 | H | O | OC$_2$H$_5$ | 65 | $n_D^{20}$: 1.5287 |
| 8 | H | H | 1 | H | NH | OC$_2$H$_5$ | 82 | 128 |
| 9 | — | — | 0 | Cl | — | (N-N pyrazolyl) | 87 | 136–137 |
| 10 | — | — | 0 | H | — | (N-N pyrazolyl) | 77 | $n_D^{20}$: 1.5057 |
| 11 | H | H | 1 | Cl | NH | —OH | | |
| 12 | H | H | 1 | Cl | NH | —O$^\ominus$½Ca$^{2\oplus}$ | | |
| 13 | H | H | 1 | Cl | NH | —O$^\ominus$Na$^\oplus$ | | |
| 14 | H | H | 1 | H | O | —N(CH$_3$)$_2$ | | 104° C. |

The herbicidal and plant-growth regulating activity of the compounds of this invention is illustrated by the following biotest Examples.

In these Examples, the compounds according to the present invention are each identified by the number (given in brackets) of the corresponding preparative Example.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denotes:

0%=no action (like untreated control);
100%=total destruction.

In this test, active compounds (1) to (10) showed a very good herbicidal activity.

EXAMPLE B

Post-emergence Test

Solvent: 5 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was then diluted with water to the desired concentration.

Test plants which had a height of 5–15 cm were sprayed with the preparation of the active compound in such a way as to apply the amounts of active compound per unit area which were prescribed. The concentration of the spray liquor was so chosen that the amounts of active compound prescribed were applied in 2,000 l of water/ha. After three weeks, the degree of damage to the plants was rated in % damage in comparison to the development of the untreated control. The figures denoted:

0%=no action (like untreated control);
100%=total destruction.

In this test, active compounds (1) to (10) showed a very good herbicidal activity.

EXAMPLE C

Inhibition of growth and defoliation and desiccation of the leaves of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 1 week, the shedding of leaves and the desiccation of the leaves were rated, in comparision with the control plants, on the following scale:

0 denotes no desiccation of the leaves, no shedding of leaves;

+denotes sight desiccation of the leaves, slight shedding of leaves;

++denotes severe disiccation of the leaves, severe shedding of leaves;

+++denotes very severe desiccation of the leaves, very severe shedding of leaves.

After 3 weeks, the additional growth of the plants was measured and the inhibition of growth was calculated in per cent of the additional growth of the control plants. 100% inhibition of growth means that growth had stopped and 0% denoted a growth corresponding to that of the control plants.

In this test, active compounds (3) to (7) and (10) showed a powerful activity.

It will be understood that the specification and examples are illustrative but not limitative of the present invention and that other embodiments within the spirit and scope of the invention will suggest themselves to those skilled in the art.

What is claimed is:

1. Phenoxybenzoic acid compound of the formula

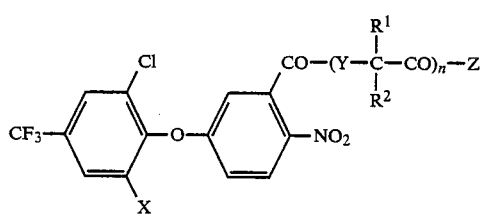

wherein
$R^1$ and $R^2$ are independently selected from hydrogen and methyl;
n is 0 or 1;
X is hydrogen or chlorine;
Y is oxygen, sulfur, imino (NH) or alkylimino (N-alkyl); and
Z is the radical

wherein
$R^3$ and $R^4$ are individually selected from optionally substituted alkyl, alkenyl, alkynyl, aryl, aralkyl and cycloalkyl, with the proviso that $R^3$ and $R^4$ can be optionally substituted alkenyl or alkynyl only when n is 1; or
$R^3$ and $R^4$ together with the N atom to which they are bonded, represent an optionally substituted, saturated or unsaturated, optionally benzo-fused mono- or bicyclic radical which optionally contains 1 to 3 further N atoms or an oxygen or sulfur atom as hetero-atoms.

2. Phenoxybenzoic acid compound as claimed in claim 1 wherein $R^1$ is hydrogen.

3. Phenoxybenzoic acid compound as claimed in claim 1 wherein n is 0.

4. Phenoxybenzoic acid compound as claimed in claim 1 wherein n is 1.

5. Phenoxybenzoic acid compound as claimed in claim 1 wherein X is hydrogen.

6. Phenoxybenzoic acid compound as claimed in claim 1 wherein X is chlorine.

7. Phenoxybenzoic acid compound as claimed in claim 1 wherein Y is oxygen.

8. Phenoxybenzoic acid compound as claimed in claim 1 wherein Y is sulfur.

9. Phenoxybenzoic acid compound as claimed in claim 1 wherein Y is imino or alkylimino.

10. Phenoxybenzoic acid compound as claimed in claim 1 wherein $R^3$ and $R^4$ are individually selected from optionally substituted alkyl, alkenyl, alkynyl, aryl, aralkyl and cycloalkyl, with the proviso that $R^3$ and $R^4$ can be optionally substituted alkenyl or alkynyl only when n is 1.

11. Phenoxybenzoic acid compound as claimed in claim 1 wherein $R^3$ and $R^4$, together with the N atom to which they are bonded, represent an optionally substituted, saturated or unsaturated, optionally benzo-fused mono- or bycyclic radical which optionally contains 1 to 3 further N atoms or an oxygen or sulfur atom as hetero-atoms.

12. Phenoxybenzoic acid compound as claimed in claim 1 wherein n is 1 and Z is an optionally substituted radicalselected from from alkoxy, alkenoxy, alkynoxy, aralkoxy and aryloxy, and hydroxy and OM.

13. Phenoxybenzoic acid compound as claimed in claim 1 designated 5-(2-chloro-4-trifluoromethyl-phenoxy)-2-nitrobenzoic acid 3,5-dimethyl-pyrazolide.

14. Phenoxybenzoic acid compound as claimed in claim 1 wherein Z is the radical
wherein

$R^3$ and $R^4$, independently of one another, each represent alkyl, cyanoalkyl, alkoxyalkyl, alkylthioalkyl or dialkylaminoalkyl, with in each case up to 10 carbon atoms, cycloalkyl with up to 12 carbon atoms, aralkyl with 1 or 2 carbon atoms in the alkyl part and 6 or 10 carbon atoms in the aryl part, which is optionally substituted by halogen, aryl with 6 or 10 carbon atoms, it being possible for the aryl radical to be substituted by 1 to 3 halogen atoms, 1 to 3 alkyl groups with in each case 1 to 4 carbon atoms, trifluoromethyl, nitro, cyano or alkoxy with 1 to 4 carbon atoms, or, provided that n represents 1, alkenyl with up to 10 carbon atoms or alkynyl with up to 10 carbon atoms, or
$R^3$ and $R^4$, together with the nitrogen atom to which they are bonded, form an optionally partially unsaturated and/or benzo-fused monocyclic or bicyclic radical which has up to 15 carbon atoms and is optionally substituted by 1 to 3 alkyl groups with in each case 1 to 5 carbon atoms or by two geminal alkoxy groups with in each case 1 to 4 carbon atoms, or is optionally substituted by a dioxanylidene or dioxanylidene radical linked in a spirocyclic-like manner, or $R^3$ and $R^4$, together with the nitrogen atom to which they are bonded, form a monocyclic radical which has up to 8 carbon atoms and is optionally substituted by 1 to 3 alkyl groups with in each case 1 to 5 carbon atoms, by phenyl, which is optionally substituted by $C_1$–$C_4$-alkyl, $C_1$–$C_4$-alkoxy, halogen, trifluoromethykl, cyano or nitro, or by benzyl or phenylethyl and is optionally saturated and optionally contains a further nitrogen atom, oxygen atom or sulphur atom, or $R^3$ and $R^4$, together with the nitrogen atom to which they are bonded, form an unsaturated five-membered heterocyclic ring which contains up to 4 ring nitrogen atoms and is optionally substituted by $C_1$–$C_4$-alkyl, $C_1$–$C_4$-alkoxy, $C_1$–$C_4$-alkylthio, phenyl, halogen, halogenomethyl, cyano, $C_1$–$C_4$-alkanoyl or $C_1$–$C_4$-carbalkoxy, or Z, provided that n presents 1, represents alkoxy, cyanoalkoxy, alkoxyalkoxy, alkylthioalkoxy, dialkylaminoalkoxy, alkenoxy or alkynoxy, in each case with up to 10 carbon atoms, aralkoxy with 1 or 2 carbon atoms in the alkyl part and 6 or 10 carbon atoms in the aryl part, which is optionally substituted by halogen, or aryloxy with 6 or 10 carbon atoms, it being possible for the aryl radical to be substituted by 1 to 3 halogen atoms, 1 to 3 alkyl groups with in each case 1 to 4 carbon atoms, trifluoromethyl, nitro, cyano or alkoxy with 1 to 4 carbon atoms.

15. Herbicidal composition comprising a herbicidally acceptable carrier and, in herbicidally effective amounts, a phenoxybenzoic acid compound as claimed in claim 1.

16. Herbicidal composition as claimed in claim 15 containing 0.1 to 95% of the active compound by weight.

17. Method of combating undesired vegetation, which method comprises applying to such vegetation or its habitat, a herbicidally effective amount of a phenoxybenzoic acid compound as claimed in claim 1.

18. Method as claimed in claim 17 wherein said phenoxybenzoic acid compound is selected from 5-(2-chloro-4-trifluoromethyl-phenoxy)-2-nitro benzoic acid 3,5-dimethyl-pyrazolide.

19. Plant growth regulant composition comprising an agriculturally acceptable carrier and, in effective amounts, a phenoxybenzoic acid compound as claimed in claim 1.

20. Method of regulating the growth of plants, which method comprises applying to the plants, or their habitat an effective amount of a phenoxybenzoic acid compound as claimed in claim 1.

21. Method as claimed in claim 17 wherein said compound is applied at a dosage of 0.05 to 10 kg per hectare.

22. Method as claimed in claim 17 wherein said compound is applied at a dosage of 0.1 to 5 kg per hectare.

* * * * *